United States Patent
Osypka

[11] Patent Number: 5,964,754
[45] Date of Patent: Oct. 12, 1999

[54] DEVICE FOR PERFORATING THE HEART WALL

[75] Inventor: Peter Osypka, Grenzach-Wyhlen, Germany

[73] Assignee: Sulzer Osypka GmbH, Grenzach-Wyhlen, Germany

[21] Appl. No.: 08/862,456

[22] Filed: May 23, 1997

[30] Foreign Application Priority Data

May 24, 1996 [DE] Germany .................... 196 21 099

[51] Int. Cl.⁶ .................................................. A61B 17/36
[52] U.S. Cl. ................................................ 606/37; 606/48
[58] Field of Search .................... 606/35, 37, 38, 606/40, 48, 49, 50; 604/164, 165, 171, 174; 607/122, 125, 126, 127, 119

[56] References Cited

U.S. PATENT DOCUMENTS

| | | | |
|---|---|---|---|
| 4,000,745 | 1/1977 | Goldberg | 607/127 |
| 4,103,690 | 8/1978 | Harris . | |
| 4,682,596 | 7/1987 | Bales et al. . | |
| 5,281,218 | 1/1994 | Imran . | |
| 5,383,874 | 1/1995 | Jackson et al. | 606/38 |
| 5,403,311 | 4/1995 | Abele et al. . | |
| 5,507,743 | 4/1996 | Edwards et al. | 606/48 |

FOREIGN PATENT DOCUMENTS

| | | |
|---|---|---|
| 0 515 867 A2 | 12/1992 | European Pat. Off. . |
| WO 93/15791 | 8/1993 | WIPO . |
| WO 95/05781 | 3/1995 | WIPO . |
| WO 96/07360 | 3/1996 | WIPO . |

OTHER PUBLICATIONS

European Search Report for corresponding European Application No. 97107093.3 dated Sep. 3, 1997 (3 pages).

*Primary Examiner*—Michael Buiz
*Assistant Examiner*—Julian W. Woo
*Attorney, Agent, or Firm*—Panitch Schwarze Jacobs & Nadel, P.C.

[57] ABSTRACT

A device (1) serves for creating perforations, borings or perfusion channels in the heart wall (2), especially in the myocardium, for generating channels running in the heart wall (2) for supplying it with blood. So that the chest cavity need not be opened in an operation for introducing such perforations, the device (1) has a catheter (4) introducible intracardially into the heart (3), which has at least one electrode or pole on its operating end and has a connection of this electrode or pole to a high frequency generator (5). Moreover, this distal operating end has at least one needle (6) insertible into the heart wall (2) from the inside, which needle functions as a coagulation tool, so that the lumen of the channel generated by it remains open and can be supplied with fresh blood from the interior of the heart (3).

19 Claims, 5 Drawing Sheets

DEVICE FOR PERFORATING THE HEART WALL

BACKGROUND OF THE INVENTION

The invention relates to a device for creating perforations, borings or channels in the heart wall, especially the myocardium, for producing channels running in the heart wall for supplying it with blood.

For treating low circulation areas of the heart muscle, creating perforations and channels from the exterior with the aid of laser beams is known, which perforations and channels after a certain time grow over again on the heart exterior, but owing to the energy of the laser beams, remain as permanent channels in the heart interior which are supplied from the interior of the heart with a part of the blood conveyed by the heart, so that in this way an improvement in the general blood supply of the heart muscle can be attained. Moreover, it has become apparent that such perforations in the heart wall generated by laser beams can even form channel-like side branches, so that creating such perforations at a certain spacing suffices to again provide a relatively large area of the heart muscle with a better blood supply.

This treatment of the heart of course requires opening the chest cavity (thoracotomy), which is not possible in every case with patients whose heart is poorly supplied with blood, because they cannot withstand a serious operation of this type under all circumstances. In addition, the heart bleeds for a while with the new operation, so that the patient also suffers a loss of blood.

Moreover, only a relatively short channel corresponding approximately to the thickness of the heart wall can be constructed, and whether in this connection a sufficient number of side branches also arise to lead to an ample blood supply is uncertain. Consequently, the surgeon is faced with the question of how many perforations of this type, and at what intervals, he must make in order to perform a successful operation.

BRIEF SUMMARY OF THE INVENTION

Underlying the invention is thus the object of creating a device for producing perforations in the heart wall of the type mentioned at the beginning, such that post-operative bleeding on the exterior and above all an opening of the chest cavity can be avoided.

The surprising solution to this contradictory object resides in the device having a catheter with an operating end which has at least one electrode or one pole and a connection of this electrode or pole to a high frequency generator, the device being intracardially introducible into the heart, and this distal operating end having a straight, curved and/or coiled needle or tool insertible several times into the heart wall from the inside as a high frequency pole or electrode.

It can thus be operated from the interior of the heart for creating perforations, borings or channels in the heart wall for improving its blood supply, since an appropriate catheter is introduced intracardially through a blood vessel, which is a technique known also from pacemaker technology. Consequently, channels may be introduced in the myocardium from the inside with a needle or a corresponding tool by multiple insertion and coagulated such that they continue to exist and do not grow together again. An opening of the chest cavity can therefore be avoided, and in addition, a complete perforation of the heart wall can also be prevented. A further advantage consists in that this catheter with its tool can also be used to coagulate troublesome tissue situated in the heart interior (ablation).

One embodiment of the invention can include a monopolar coagulation needle being provided as an operating end or tool, and a second indifferent (i.e., ground) electrode for outside application on a patient being connectable with a high frequency generator.

A modified embodiment can provide that a bipolar coagulation needle is provided as an operating end, which has electrodes or poles which are spaced from and insulated against each other, both being connected or connectable with the high frequency generator. In the latter case, the ground electrode applied outside on the patient can be dispensed with, in which area burns can occur under certain conditions.

It is especially expedient if the needle or the tool is insertible or retractable into the distal end of the catheter, and is extendible out of it for sticking into the inside of the heart wall. The catheter can consequently, first of all, be introduced into the interior of the heart through a blood vessel, while the needle or the tool is still retracted, so that injuries to the vessel owing to this tool can thus be avoided. Once the catheter has reached the place in the interior of the heart to be perforated with its distal end, the needle, which is displaceable approximately axially, can be introduced into the heart wall, and in such a manner that this is not completely pierced. In the coagulation process, taking place at the same time or then following, the perforation can be made into a permanent channel.

It is especially beneficial for obtaining the longest channels possible within the heart wall, thus for obtaining channels which can even be longer than the heart wall is thick, if the curved needle forms approximately a quadrant up to a semicircle, or perhaps even more than a semicircle. A curvature of the needle over approximately a semicircle or even exceeding this can lead to channels which are open on both ends to the interior of the heart. It is also possible, however, on account of the flexibility of the needle or the tool, to introduce this into the heart wall such that the curvature is partially eliminated in the operating position so that the free end does not emerge again from the heart wall, so that a correspondingly even longer channel arises which, aside from its entry from the inside into the heart wall, runs over a relatively great length in the interior of the heart wall between its inner and outer sides.

In order to avoid a complete piercing of the heart wall, the displacement path of the needle or tool relative to the distal end of the catheter can be less than the thickness of the heart wall. Other or additional measures can also be provided, however.

For example, the needle can be elastic and precurved and transform into its curved shape upon extension out of the distal end of the catheter. It can then be longer without piercing the heart wall, because it creates a curved perforation into the heart wall extending from the distal end of the catheter, which enters obliquely and curved into the heart wall, and does not penetrate through the heart wall owing to the curvature of the tool. A complete piercing of the heart wall can thereby be avoided and a longer channel for blood supply can be created at the same time.

A further advantageous and expedient configuration of the invention can consist of the coagulation needle or similar tool being rotable relative to the catheter. The continuation of the needle at the proximal end of the catheter can, for example, have a turning grip, so that the user can rotate the needle in a desired form which is suitable in connection with its precurvature. For example, following an initial insertion and coagulation a precurved needle of this type can be withdrawn from the channel created by it, then be rotated within the catheter, and then be inserted again into the myocardium with a somewhat modified direction so that several channels to be perfused with blood can be generated at the same spot on the interior heart wall, which are arranged approximately opposed to each other or in a star form. Thus, a large area blood perfusion can be achieved early and rapidly, even if individual ones of the channels generated are not supposed to form additional side branches.

The needle or similar coagulation tool can be constructed as a screw coil with especially sharpened end. Consequently, a correspondingly coiled, and thus relatively longer channel can be created with it, even though only a relatively small thickness of the heart wall is available. In addition, there also results thereby a fixation of the catheter, so that a disturbance of the coagulation process owing to a heart beat can be better avoided.

A configuration of the invention modified in relation to this can provide that, in addition to a straight or curved needle or similar coagulation tool, a screw coil surrounding the tool's its exit from the catheter is provided for fixing the catheter end on the inside of the heart wall. In this case, the distal catheter end can be fixed in place with the aid of the screw coil, so that the heart movements cannot have an unfavorable effect on the perforation process to be executed by the coagulation needle proper.

At the same time, it is possible to construct this holding coil, provided in addition to the needle or the like, as an additional electrode as well, or as an additional coagulation tool, and to connect it with the high frequency generator, such that each application process of the catheter thus leads to several perforations at the same time, whereby moreover the catheter is well fixed on the inside of the heart wall.

The coagulation tool can be a hollow needle or a cannula, in whose interior in particular a conduit can run to a temperature sensor arranged on its tip or near its tip, and the temperature sensor can be connected with a temperature indicator and/or a control or regulator for the high frequency generator. Consequently, during coagulation of the channel in question, the temperature can be monitored, and an excessively sharp rise in temperature can be avoided, possible automatically. In addition, a contrast medium can be introduced through the hollow needle or cannula in order to monitor the course of perforation. The thickness of the heart wall can thus especially be exploited as best as possible in creating the channel, without completely piercing the heart wall.

Another or an additional possibility for controlling the depth of penetration of the needle or the tool into the myocardium can consist of an ultrasonic generator being arranged on the distal end of the catheter in the area of the exit of the needle for measuring the thickness of the heart wall and the depth of penetration of the needle or the like.

A further configuration of the invention can consist of the needle or cannula being insulated on its exterior from its exit from the distal end of the catheter up to near to its tip, so that only the tip itself is bare and constructed as a coagulation area. In this way, it is possible that a coagulation can already be conducted upon introducing the needle, and this then operates only in the area in which the needle tip is exactly situated; that is, the channel created by the perforation is respectively exposed to the high frequency at each of its points for approximately an equal length of time. There consequently results a uniform coagulation on the interior wall of the artificial channel thereby constructed in the heart wall.

A further advantage of the construction of the needle as a hollow needle or cannula furthermore consists in that fluid samples can be taken through this needle, or medications can be injected.

In sum, there results a device with which perforations can be durably created in the heart wall without having to open the chest cavity. In a surprising way, a proven technique is relied upon, namely that of providing a catheter introducible to the inner heart wall, which with an appropriate operating end can penetrate into the heart inner wall, so that then through the coagulation, also known per se, the perforation can be made into a durable channel supplied with blood from within. Post-operative bleeding on the exterior of the heart is effectively avoided at the same time. Since a serious chest cavity operation is avoided, even the hearts of patients who could not endure a severe operation of this type can be provided with holes and channels for supplying fresh blood from the heart chamber.

BRIEF DESCRIPTION OF THE SEVERAL VIEWS OF THE DRAWING

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, partly in schematic representation.

DETAILED DESCRIPTION OF THE INVENTION

Figure 1:
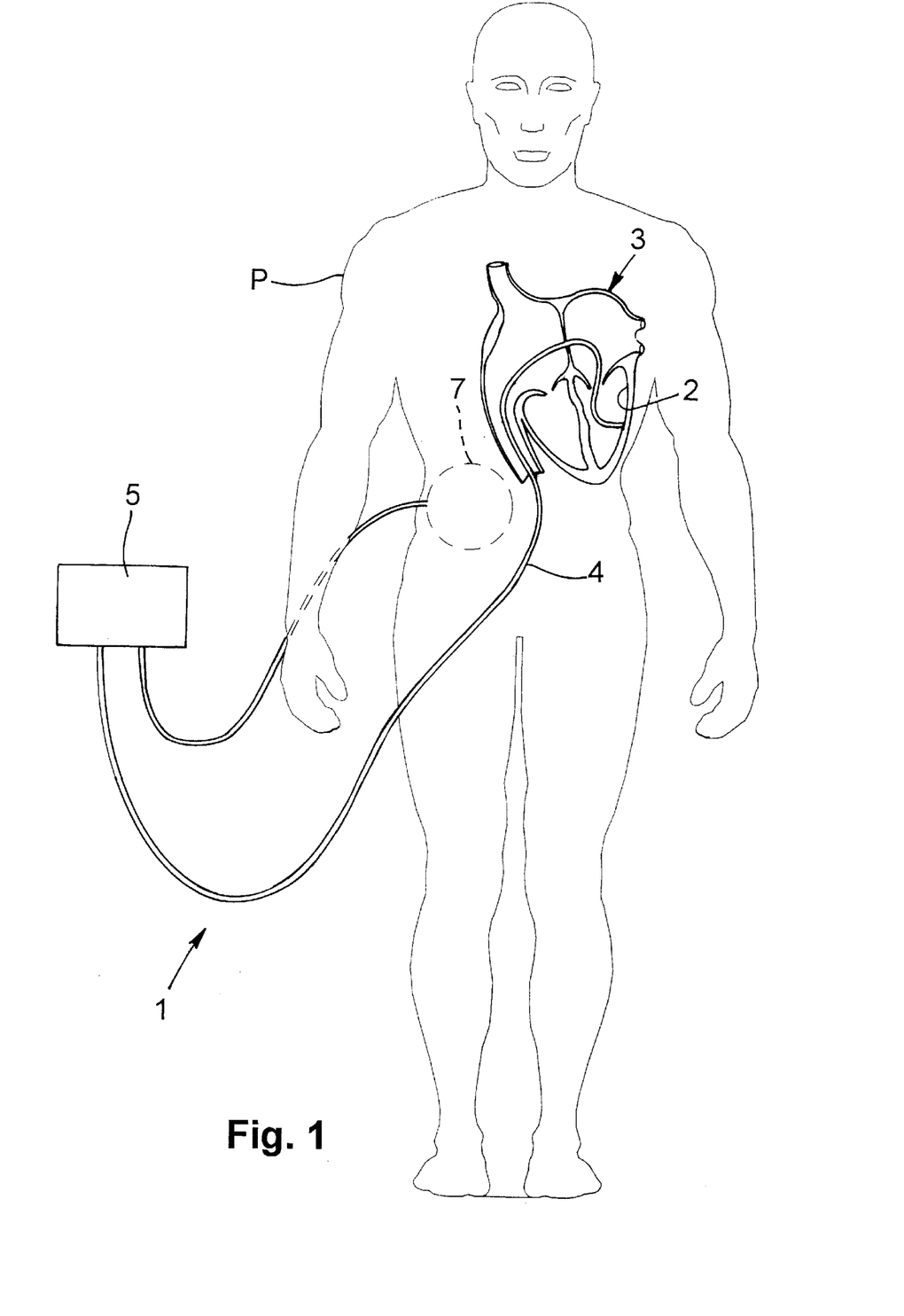
FIG. 1 shows a catheter which is introduced intracardially into the heart of a patient and which impinges upon the interior of the heart with its operating end, wherein the opposite end is connected to a high frequency generator to which is connected in addition, moreover a ground electrode which is in contact with the patient.

A device, designated as a whole with 1, schematically represented overall in FIG. 1, serves to create perforations, holes or channels in the wall 2 of a heart 3, also referred to herein as the heart wall or myocardium 2. In this way, channels running in the heart wall 2 can be generated through which the heart wall can be supplied with fresh blood from the interior of the heart; that is, the heart wall can be better infused with blood if channels of this type are introduced with the device 1 in a manner to be described below.

Figure 2:
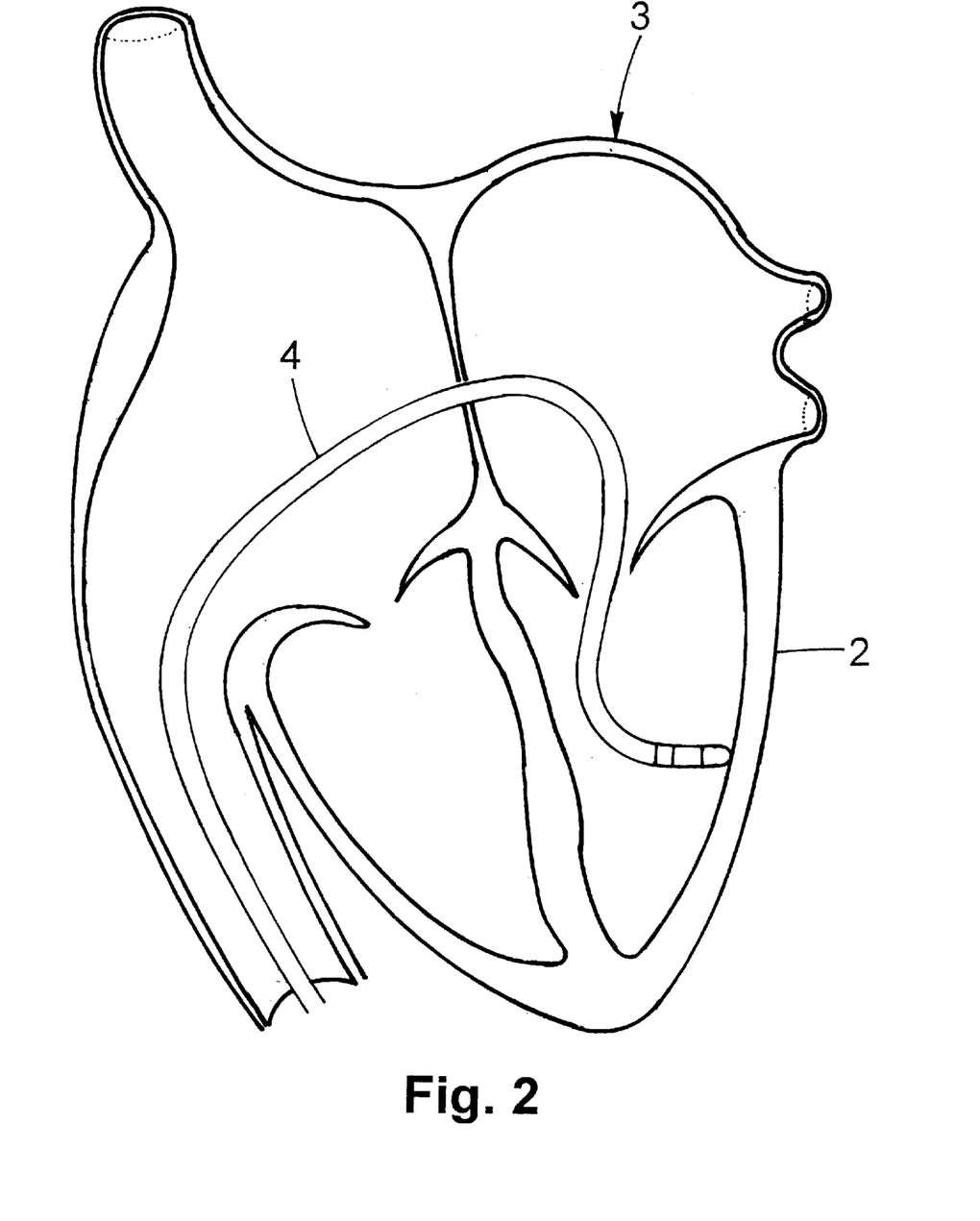
FIG. 2 shows on an enlarged scale, a longitudinal section through the heart, in which the distal end of the catheter is introduced with its operating end.

The device 1 chiefly has, first of all, a catheter 4 with an operating end which has at least one electrode or one pole and a connection of this electrode or pole to a high frequency generator 5 and is introducible intracardially into the heart in accordance with FIG. 1 and 2. The distal operating end mentioned has, in accordance with FIGS. 3 to 10, at least one straight, curved and/or coiled needle 6, thus a performation tool, which can be stuck into the heart wall 2 from the inside, as a high frequency pole or electrode. This coagulation tool in the form of a needle 6 can therefore be stuck into the heart wall 2 from the inside after introducing the catheter 4 into the interior of the heart 3, as clarified or represented in FIGS. 2 thru 10, whereupon or whereafter a coagulation of this boring or perforation is conducted with the aid of the high frequency generator 5, so that it remains permanently and does not heal again. Consequently, fresh blood can enter from the interior of the heart 3 into the perforation so constructed and thereby supply the heart wall 2 with blood at this spot.

In the embodiments represented, a monopolar coagulation needle 6 is provided as an operating end or coagulation tool, and in accordance with FIG. 1, there is connected with the high frequency generator 5 a second, ground electrode 7 for exterior application to a patient P.

Also conceivable would be a bipolar coagulation needle 6 as the operating end, which could have electrodes or poles spaced from each other and insulated against one another, both being connected or connectable with the high frequency generator 5.

Figure 3:
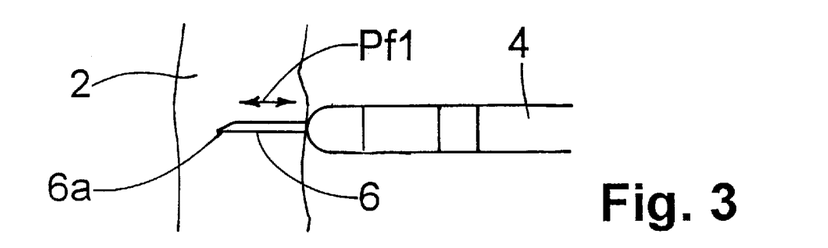
FIG. 3 shows, on still further enlarged scale, the operating end of the catheter with an advanceable and retractable needle, inserted into the heart wall from the inside, constructed as an electrode for creating a perforation in the heart wall.
Figure 4:
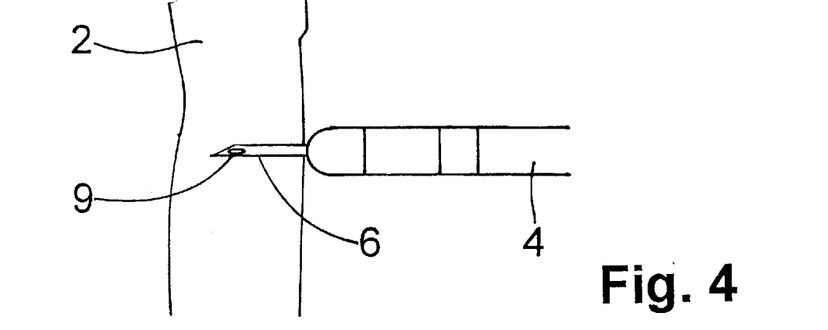
FIG. 4 is a representation corresponding to FIG. 3, in which the coagulation needle has a temperature sensor near its tip.

In FIG. 3, the double arrow Pf1 indicates (which also applies for the remaining embodiments) that the needle 6 is insertible or retractable into the distal end of the catheter 4 and is extendible out of it for sticking into the inside of the heart wall 2, wherein the extended position is represented in all figures. Moreover, one also recognizes in all figures that the displacement path of needle 6, relative to the distal end of the catheter 4, is less than the thickness of the heart wall 2 whereby in accordance with FIG. 6, 9 and 10, the needle 6 can also be elastic and precurved, so that it evolves into its curved form upon extension from the distal end of the catheter, and then indeed can have a longer total length than corresponds with the thickness of the heart wall 2, wherein, however, the measured length or extension of this needle in the continuation direction of the catheter 4 is still less than the thickness of the heart wall 2, so that in all these cases, completely piercing the heart wall 2 is avoided. Consequently, an escape of blood to the outside of the heart 3 is avoided.

Figure 9:
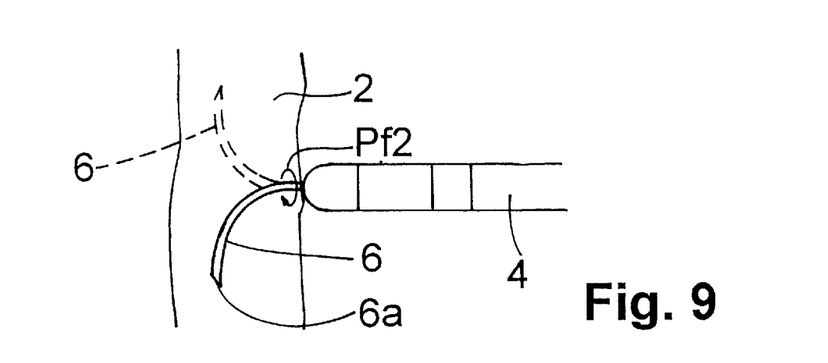
FIG. 9 shows an embodiment with a precurved needle which, in addition, is rotably arranged in the catheter.

In accordance with FIG. 9, the needle 6 or similar coagulation tool can be rotable relative to the catheter 4, wherein the pivot bearing and rotation activation are not represented in greater detail, because they can be carried out with known means as are also known from other operating tips which are rotable relative to a catheter. In this way, it is possible in accordance with FIG. 9, first of all, to extend the needle 6 and create a channel in the heart wall which curves downwardly in the represented figure, subsequently to withdraw the needle into the catheter 4, rotate it in accordance with the curved arrow Pf2, and stick it again into the heart wall while the position of the catheter 4 remains the same, so that with an identical entry opening, two branching perforations or channels result. The precurvature of the needle 6 is thus, eliminated upon retraction against spring tension, owing to its elasticity, so that the needle 6 finds space within the catheter 4 despite this curvature. Nevertheless, the length and shape of the curvature can also go approximately to a semicircle in accordance with FIG. 10, so that when the needle 6 is extended sufficiently far, its tip 6a can emerge again out of the heart wall 2 into the interior of the heart 3, in order to permit an even better blood infusion under certain conditions.

Figure 5:
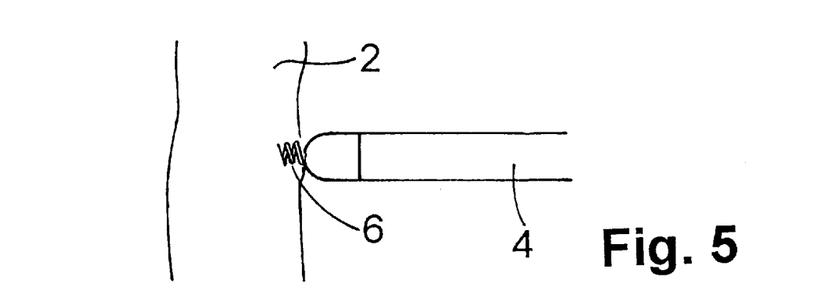
FIG. 5 shows an embodiment in which the needle is built as a coil.

In the embodiment in accordance with FIG. 5, that the needle 6 can also be constructed as a screw coil with an especially sharpened end is represented. It thereby fulfills a double function, as it generates the desired helix-like perforation in this case when introduced into the heart wall, and fixes the catheter 4 and itself during the coagulation process, so that heart movements cannot lead to unwanted displacements or even to a reemergence of the needle 6 from the heart wall.

Figure 6:
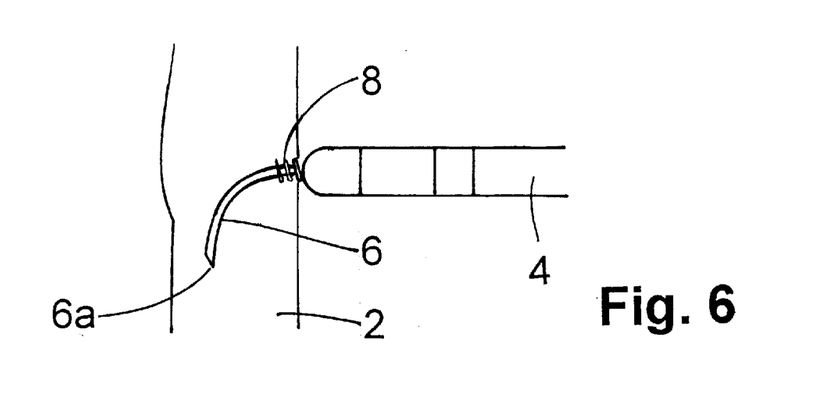
FIG. 6 shows an embodiment in which a curved and retractable needle and a screw coil are arranged on the distal end of the catheter, wherein the curved needle extends approximately over a quadrant.

Indeed, a precurved needle 6, which assumes its curved position upon extension out of the catheter 4 and insertion into the heart wall 2, also creates a certain fixation on account of this profiling. Nonetheless, it is moreover possible to provide in addition to a straight or curved needle 6 a screw coil 8 which surrounds the needle's exit from the catheter 4 for fixation of the catheter end on the inside of the heart wall 2, as is represented in FIG. 6. Consequently, the catheter 4 can be fixed with the aid of the screw coil 8, while the curved needle 6 in this case is or will be inserted into the heart wall 2, and should remain there during the coagulation period.

Nevertheless, this holding coil 8 provided in addition to the needle 6 can, if need be, itself be constructed as an additional electrode and as an additional coagulation tool, and be connectable or connected with the high frequency generator 5. There results then practically a combination of embodiments in accordance with FIG. 5 and 9, wherein, however, even a straight running needle 6 can be combined with such a holding coil 8.

Figure 7:
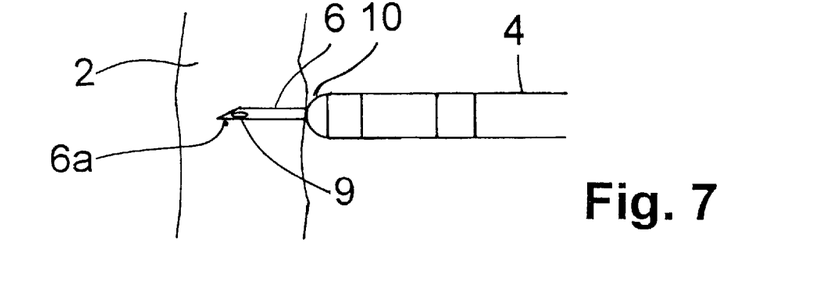
FIG. 7 shows an embodiment in which an ultrasound sensor for ascertaining the thickness of the heart wall and the penetration depth of the coagulation needle is arranged on the distal end of the catheter.

The coagulation needle 6 can be a hollow needle or cannula, so that therewith contrast media for examination of the channel created to serve for blood supply is also possible, or medications can be injected, or fluid samples can be taken. In FIG. 7, it is indicated that close to the tip 6a of such a needle 6 a temperature sensor 9 can be arranged, for which then, in the interior of the hollow needle 6, a conduit can run from this temperature sensor 9 to a temperature indicator and/or to the control or regulator of the high frequency generator 5, so that the coagulation process and especially the temperature arising in connection with it can be monitored and, if necessary, be automatically controlled or regulated. Consequently, too low or too high temperatures can be avoided.

It is moreover indicated in FIG. 7 that an ultrasonic generator 10 can be installed on the distal end of the catheter 4 in the area of the exit of the needle 6 for measuring the thickness of the heart wall 2 and the penetration depth of the needle 6, for which purpose this could also be realized in other embodiments.

Figure 8:
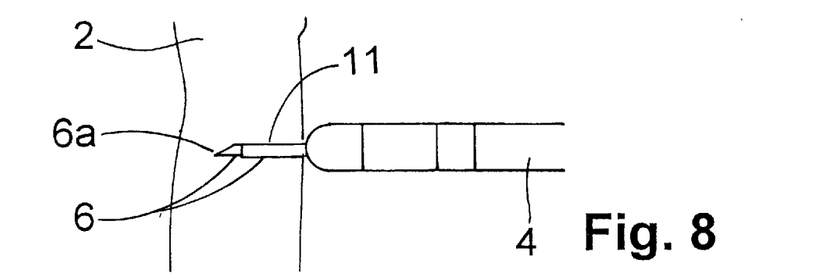
FIG. 8 shows an embodiment in which the coagulation needle is insulated over the major portion of its length, so that its tip only is constructed bare for coagulation in the tip area.

FIG. 8 depicts an embodiment in which the needle 6 is enclosed on its exterior from its exit from the distal end of the catheter 4 to near its tip 6a with an insulation 11, so that only the tip 6a itself is bare and constructed as a coagulation area. Consequently, the coagulation process can be conducted already during introduction of the needle 6 and progress in correlation with the advance of the needle 6. Influence can be exerted on the intensity of coagulation by selection of the rate of advancement.

Channels in the myocardium 2 of the heart 3 necessary for revascularization can thus be created in a simple manner without employing a thoracotomy, whereby in an advantageous manner, a controllable, intracardially or transvenously introducible catheter 4 generates such channels from the interior of the heart up to a certain depth and without completely piercing the heart wall 2. In this connection, the catheter 4 can first of all be positioned in the heart 3 in the usual manner, whereafter an appropriate needle 6, cannula or similar coagulation tool can emerge from the catheter's operating end and penetrate to controlled depths of the myocardium. The positioning of the operating end of the catheter 4 can be undertaken by measurement of intracardial EKGs. After this, a current output takes place by means of a high frequency generator 5 through the needle 6 in relation to a large surface ground electrode 7, which, for example, can be applied to the back of the patient P. This has the result that the channel created by the needle 6 is partially coagulated, and its lumen thereby remains open in the myocardium 2. Since with the aid of a bent needle 6, even correspondingly long and curved channels or perfusion holes can be created, correspondingly longer "artificial" vessels result for blood supply of the myocardium. Above and beyond this, the device 1 can also be used for high frequency ablation, based on the connection with the high frequency generator 5.

The already mentioned extendibility and retractability of the needle 6 is represented even more clearly in FIG. 11 in individual steps. For this purpose, there is used in this case a curved needle 6, perhaps according to FIG. 10. This is first of all advanced out of the catheter in accordance with arrow Pf2, whereby a further displacement in accordance with arrow Pf3 leads to the needle 6 assuming its curved position. If the catheter 1 is used in this position, one would practically have a needle curved approximately around a quarter circle.

Figure 10:
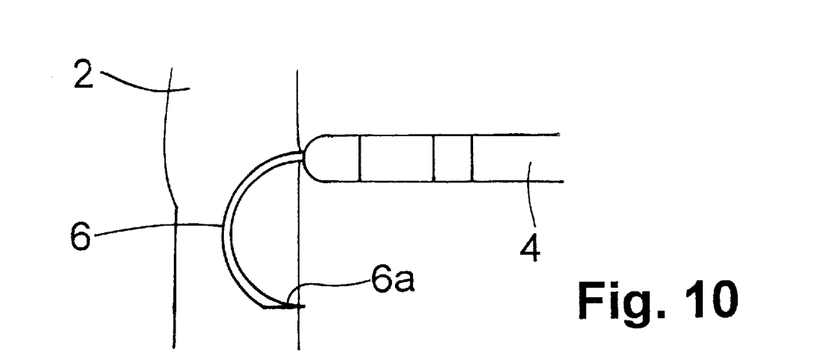
FIG. 10 shows an embodiment with a curved needle which extends almost over a semicircle, and is so long that it pierces the inside of the heart wall a second time with its free end.
Figure 11A:
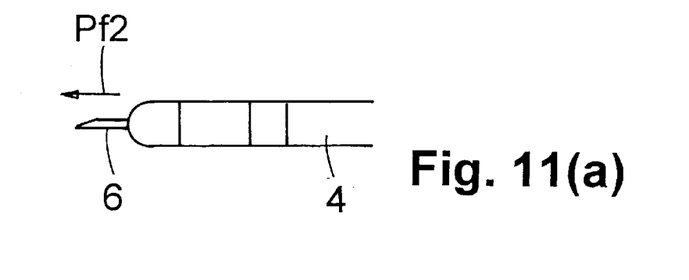
FIG. 11 shows an embodiment with a precurved needle which, first of all, is more and more extendible out of the catheter until it extends approximately over a semicircle, and then is retractable again later in the same manner, wherein individual intermediate positions of this extendibility and retractability are represented one under the other in FIG. 11.
Figure 11B:
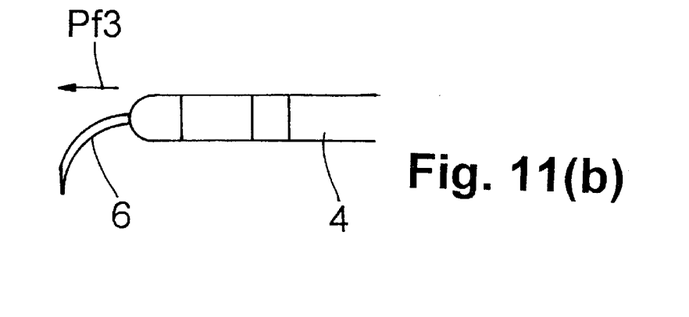
Figure 11C:
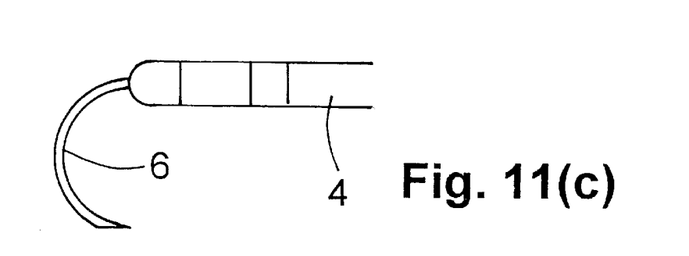
Figure 11D:
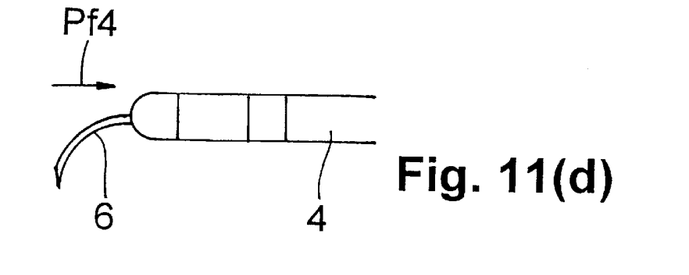
Figure 11E:
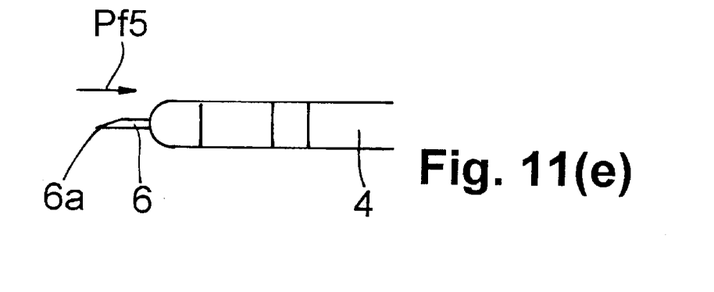

The further extension finally leads to the needle 6 extending over its predetermined half circle, as represented in FIG. 10. This middle representation in FIG. 11 thus corresponds to the operating form. The previously reached position could, on the other hand, correspond to a usage according to FIG. 9.

From this position, the needle can then first of all be retracted partially in accordance with arrow Pf4, and then again completely withdrawn in accordance with arrow Pf5. Moreover, the withdrawal can go so far that the needle 6 completely disappears in the catheter 4. However, a piece, and especially the tip 6a, can jut out, if desired, in order to facilitate the operating process of insertion. This process in accordance with FIG. 11 can, if necessary, be repeated several times in order to create an appropriate number of heart channels from the inside of the heart.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device (1) comprising a catheter (4) with a distal operating end having at least one electrode or pole and a connection between said electrode or said pole and a high frequency generator (5), said catheter being introducible intracardially into a heart (3), wherein said electrode or said pole on said distal operating end includes at least one needle (6) which can be inserted into a heart wall (2) from its inside, said at least one needle being retractable into said distal end of said catheter (4) and being extendable for sticking into the heart wall, said needle (6) being elastic and precurved, and transforms into a curved shape upon said needle being extended out of said distal end of said catheter (4) to generate channels running in the heart wall (2) for providing the heart wall with blood.

2. The device according to claim 1, wherein said needle comprises a monopolar coagulation needle (6), and a second, ground electrode (7) is provided for external application on a patient (P) and is connectable with the high frequency generator.

3. The device according to claim 1, wherein said needle comprises a bipolar coagulation needle (6) which has two electrodes spaced from each other and insulated against each other, both said electrodes being connectable with the high frequency generator (5).

4. The device according to claim 1, wherein the curved shape of said needle forms approximately more than a half circle.

5. The device according to claim 1, wherein said needle is rotatable relative to said catheter (4).

6. The device according to claim 1, wherein a screw coil (8) surrounds an exit of said needle from said catheter (4), said coil (8) enabling fixation of the distal operating end of said catheter on the inside of the heart wall (2).

7. The device according to claim 6, wherein said coil (8) and said needle (6) are both constructed as electrodes for coagulation and are connectable with the high frequency generator (5).

8. The device according to claim 1, wherein said needle is hollow and has a temperature sensor arranged at approximately a tip of said needle, said temperature sensor having a connection with a temperature indicator and/or a control or a regulator for the high frequency generator (5), wherein said connection runs in an interior of the hollow needle.

9. The device according to claim 1, wherein an ultrasonic generator (10) is arranged on the distal operating end of said catheter (4) in a region of an exit of said needle (6), said ultrasonic generator being capable of measuring at least one of a thickness of the heart wall (2) and a penetration depth of said needle (6).

10. The device according to claim 1, wherein said needle (6) is insulated on an outside of said needle from an exit of said needle from the distal operating end of said catheter (4) up to approximately a tip (6a) of said needle (6), such that only said tip (6a) is bare and constructed as a coagulation region.

11. A device (1) comprising a catheter (4) with a distal operating end having at least one electrode or pole and a connection between said electrode or said pole and a high frequency generator (5), said catheter being introducible intracardially into a heart (3), wherein said electrode or said pole on said distal operating end includes at least one tool (6)

which can be repeatedly inserted into a heart wall (2) from its inside to generate channels running in the heart wall (2) for providing the heart wall with blood, a displacement path of said tool relative to the distal operating end of said catheter being adapted to be less than a thickness of the heart wall, and wherein said tool is rotatable relative to said catheter.

12. The device of claim 11 wherein the tool comprises a monopolar coagulation needle (6), and a second, ground electrode (7) is provided for external application on a patient (P) and is connectable with the high frequency generator.

13. The device according to claim 11, wherein said tool comprises a bipolar coagulation needle (6) which has two electrodes spaced from each other and insulated against each other, both said electrodes being connectable with the high frequency generator (5).

14. The device according to claim 11, wherein a screw coil (8) surrounds an exit of said tool from said catheter (4), said coil (8) enabling fixation of the distal operating end of said catheter on the inside of the heart wall (2).

15. The device according to claim 14, wherein said coil (8) and said tool (6) are both constructed as electrodes for coagulation and are connectable with the high frequency generator (5).

16. A method of generating channels running in a heart wall (2) for providing the heart wall with blood, comprising:

introducing a catheter (4) intracardially into a heart (3) of a patient;

extending a high frequency pole or electrode in a form of a needle from a distal end of said catheter (4) and sticking said needle into the heart wall from inside of the patient's heart;

channels running in the heart wall (2) with said needle for providing the heart wall with blood; and transmitting high frequency energy to said needle from a high frequency generator connected to said needle for coagulation, forming permanent channels.

17. The method of claim 16 further comprising:

directing said needle in a direction in the heart wall such that said needle travels in a path between inner and outer sides of the heart wall to form the channel with a relatively long length.

18. The method of claim 16 further comprising:

providing a screw coil (8) around an exit of said needle from said catheter (4); and fixing the distal operating end of said catheter on the inside of the heart wall (2) using said screw coil prior to extending said needle from the distal end of said catheter.

19. The method of claim 16 further comprising:

providing a curved needle which transforms to a curved shape as said needle extends from the distal end of said catheter.

* * * * *